Figure 1:
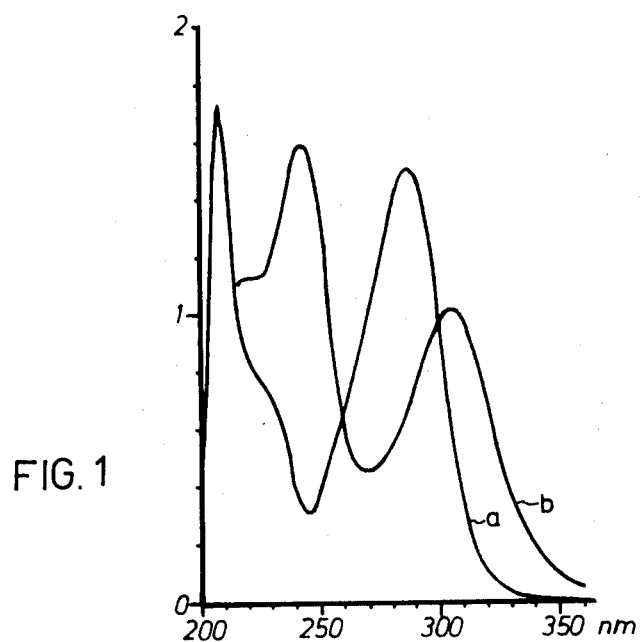

United States Patent [19]

Hagenmaier et al.

[11] 4,315,922
[45] Feb. 16, 1982

[54] NIKKOMICINS, A PROCESS FOR THEIR PREPARATION AND THEIR USE AS AGENTS FOR COMBATING PESTS

[75] Inventors: Hans-Paul Hagenmaier, Tübingen; Wilfried König, Pinneberg; Hans Zähner; Hans-Peter Fiedler, both of Tübinger; Wolfgang Dehler, Dettenhausen; Adelinde Keckeisen, Tübingen; Hartwig Holst, Pohlheim; Gerhard Zoebelein, Leverkusen, all of Fed. Rep. of Germany

[73] Assignee: Bayer Aktiengesellschaft, Leverkusen, Fed. Rep. of Germany

[21] Appl. No.: 167,291

[22] Filed: Jul. 10, 1980

[30] Foreign Application Priority Data

Jul. 12, 1979 [DE] Fed. Rep. of Germany ....... 2928137

[51] Int. Cl.³ .................. A61K 31/71; C07H 19/06
[52] U.S. Cl. .................................. 424/181; 424/180; 536/23
[58] Field of Search ................. 424/181, 180; 536/23

[56] References Cited

U.S. PATENT DOCUMENTS 4,046,881 7/1977 Dähn et al. ........................ 424/81
4,158,608 6/1979 Dahn et al. .

FOREIGN PATENT DOCUMENTS 2701890 7/1978 Fed. Rep. of Germany .
13766 12/1979 Fed. Rep. of Germany .

Primary Examiner—Blondel Hazel
Attorney, Agent, or Firm—Sprung, Felfe, Horn, Lynch & Kramer

[57] ABSTRACT

Pesticidally active substantially pure nikkomicin fractions obtained from *Streptomyces tendae* Ettlinger et al Tü0 901, the fractions being selected from the group consisting of a mixture of nikkomicin I and J, and a mixture of nikkomicin M and N.

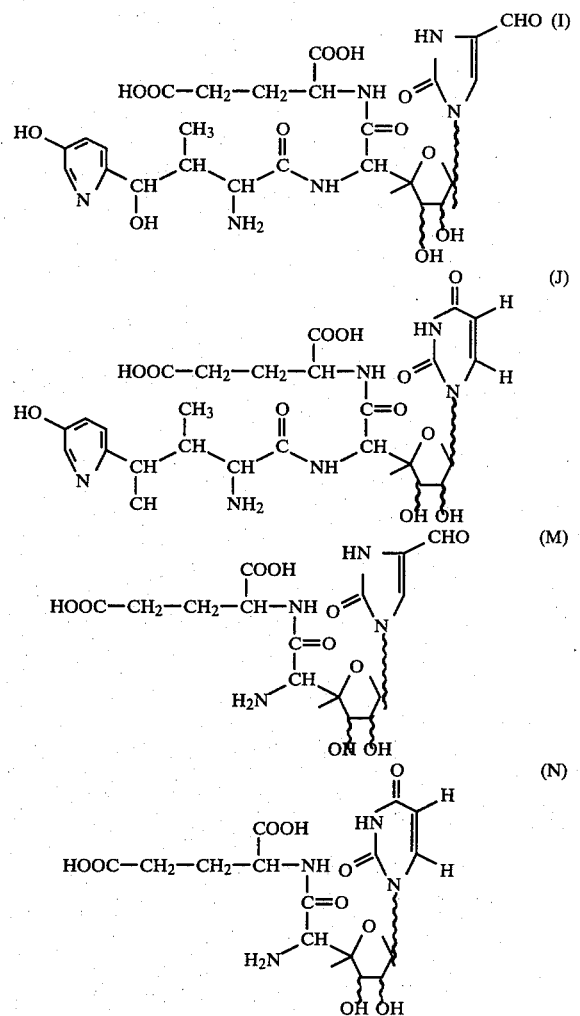

12 Claims, 18 Drawing Figures

NIKKOMICINS, A PROCESS FOR THEIR PREPARATION AND THEIR USE AS AGENTS FOR COMBATING PESTS

The present invention relates to certain new nikkomicins, to a microbiological process for their preparation from Streptomycetes strains and to their use as agents for combating pests.

It has already been disclosed that polyoxines have found a wide application in plant protection as fungitoxic agents. However, the disadvantages of these compounds are that they are unstable to alkali and also that they occur only as mixtures of varying composition and are thus difficult to meter and standardize exactly.

Furthermore, an antibiotic called nikkomicin, which has a powerful fungicidal action against phytopathogenic fungi, is known from U.S. Pat. No. 4,046,881.

It has now been found that this nikkomicin consists of several structurally different components, and that the components or groups of components of the nikkomicin mixture are suitable as agents for combating pests.

The nikkomicins and the mixture consisting of several components are produced by submerse culture of suitable micro-organisms in suitable nutrient solutions under suitable physical conditions. They are separated off from the culture solution by adsorption and precipitation and are concentrated by further suitable methods.

The strain Streptomyces tendae Ettlinger et al. Tü 901 of the order of the Actinomycetales, family Streptomycetaceae, genus Streptomyces, can be employed for the preparative process. This strain was isolated from a soil sample from Nikko, Japan. It has been stored under the No. CBS 354.75 in the Centraalbureau voor Schimmelkultures Central Bureau of Mould Cultures), Baarn, Netherlands; under the No. ATCC 31160 in the American Type Culture Collection, Rockville, Md., U.S.A.; and under the No. FRI 3136 in the Fermentation Research Institute, Osaka, Japan. This strain belongs to the genus Streptomyces and is characterized by the following properties:

(a) The spores ae ellipsoidal. They are $0.4$–$0.6 \times 1$–$.2$–$1.4\mu$ in size and have a smooth surface.
(b) The air mycelium is initially chalk-white in color, and in the ripened state is ash-gray (cinereous).
(c) The spore chains are monopodially branched and are arranged in loose spirals and loops.
(d) A black pigment was formed on peptone-iron-agar at 27° C. The strain is chromogenic.

The determining characteristics summarized identify the strain Tü 901 as belonging to the species Streptomyces tandae Ettlinger.

Nutrient media which contain the customary sources of carbon and nitrogen and the necessary salts are used for the process for the preparation of the nikkomicin mixture. The following compounds can be used as the source of carbon: carbohydrates, in particular polysaccharides, for example starch, disaccharides, for example maltose and sucrose, and monosaccharides, for example glucose and fructose. Furthermore, it is also possible to use sugar alcohols, for example mannitol and glycerol, and in addition also naturally occurring mixtures, for example malt extract. The customary sources of nitrogen can be used as the source of nitrogen, for example protein substances, albumin hydrolyzates, aminoacids, ammonium ions, nitrates, naturally occurring complex substances, such as peptones, casein hydrolyzates, "corn-steep liquor", soya bean flour and meat extract, and suitable mixtures thereof.

The salts, for example phosphates, sulphates or chlorides, of magnesium, iron, zinc and manganese are preferably used as auxiliaries in the nutrient medium. The concentration of these substances can vary within wide limits, and in some cases the necessary concentrations are contained as impurities in the above-mentioned sources of carbon or nitrogen or in the water used.

Furthermore, anti-foaming agents of the most diverse nature can also be used as auxiliaries, for example soya bean oil, polyols or silicones. Buffers, including organic buffers, may be used to maintain a desired pH range.

Water may be mentioned as the most important diluent for the nutrient media.

The preparative process is in general carried out under aerobic conditions; the organisms can be cultured by customary methods, for example using shaken cultures or aerated fermentation cultures. The percentage proportions of the constituents of the nutrient solution can vary within wide limits, and in general the sources of carbon make up 1 to 10% by weight, preferably 2 to 5%, and the sources of nitrogen make up 0.1 to 4% by weight, preferably 0.5 to 2%; the salts may be present in the customary concentrations, preferably in the range between 0.01 and 1 percent by weight. The anti-foaming agents are generally present in a concentration of 0 to 1% strength. The temperatures used for the sterilization are in general, 100° to 140° C., preferably 120° to 130° C.

The pH values of the growing cultures are, in general 5.5 to 8, preferably 7 to 7.5. The culturing temperature can, in general, be between 18° and 37° C., and is preferably 27° to 30° C. It has been found that the amount of antibiotic becoming more concentrated in the culture broth in general achieves its maximum about 1 to 14, preferably, about 3 to 5 days after the culture is started. The end point of the incubation is established with the aid of biological tests, and in particular the action against Botrytis cinerea (test method according to R. Hütter et al., Arch. Mikrobiol, 51 1–8 [1965]) and Mucor hiemalis (test method according to the dissertation of G. Kirst, Tübingen [1971], and furthermore according to Kneifel et al., J. Antib. A 27, 20–27 [1964]) is established.

In carrying out the preparative process, the culture solutions can be worked up by first carrying out a filtration, whereupon the mycelium is separated off. The latter can be subjected to ion exchange chromatography on suitable exchangers. The chromatography can be carried out in the form of column chromatography or of preparative thin-layer chromatography. Any of the customary inorganic or organic adsorbents can be employed as the adsorbents, for example aluminum oxide, silica gel, magnesium silicate, active charcoal, cellulose, cellulose derivatives, synthetic resins, such as polyamides and derivatives of polyamides and the like, for example acetylated polyamide, or dextran gels. The most diverse solvents or solvent mixtures in which the antibiotic according to the invention is soluble can be used as the running agent in the case of preparative thin layer chromatography. Gel chromatography and isolation of the pure compound on a further column with subsequent freeze-drying can then be carried out.

Figure 2:
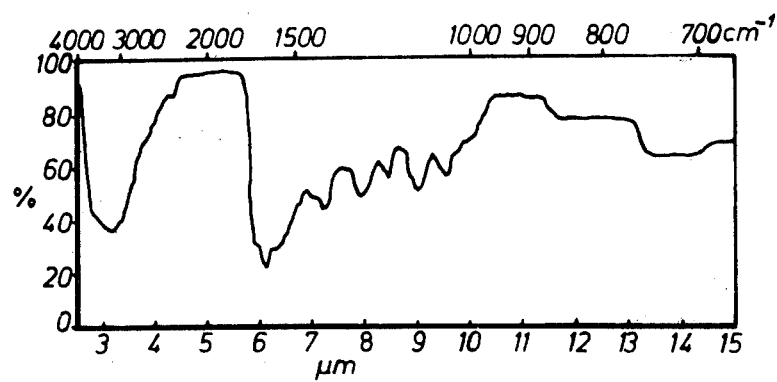
Figure 3:
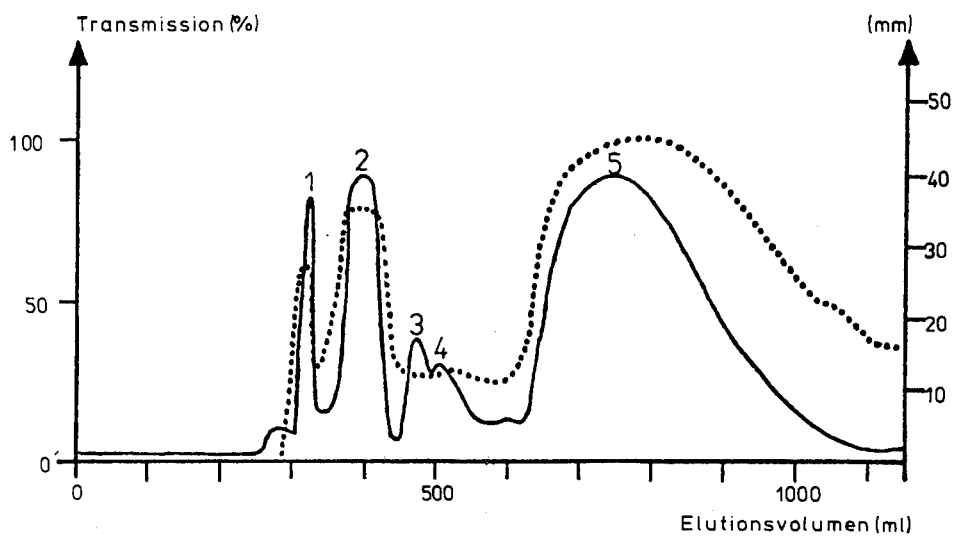
Figure 4:
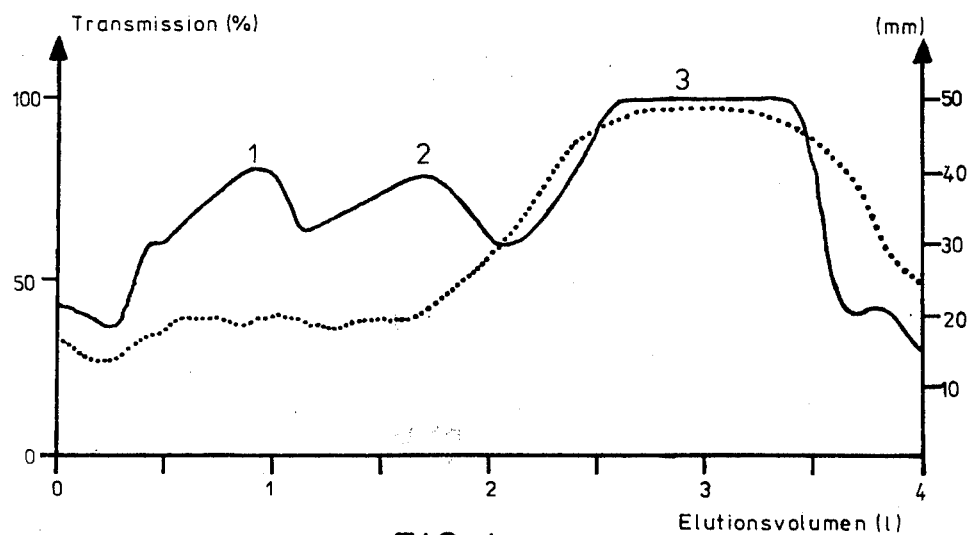
Figures 5, 6:
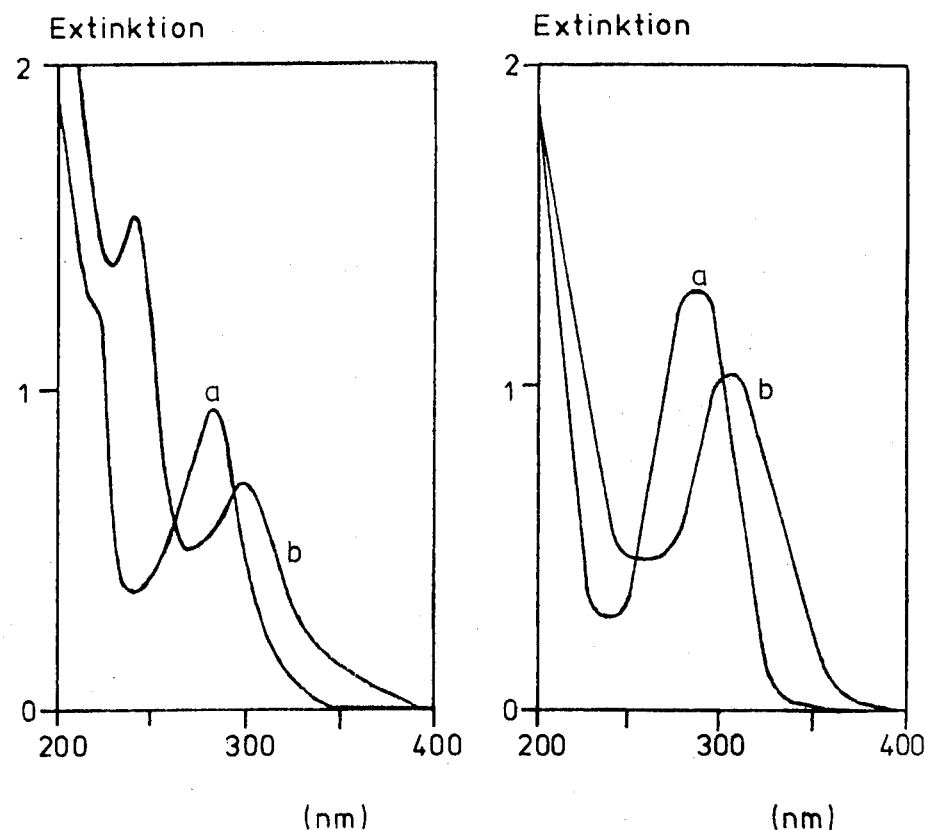
Figures 7, 8:
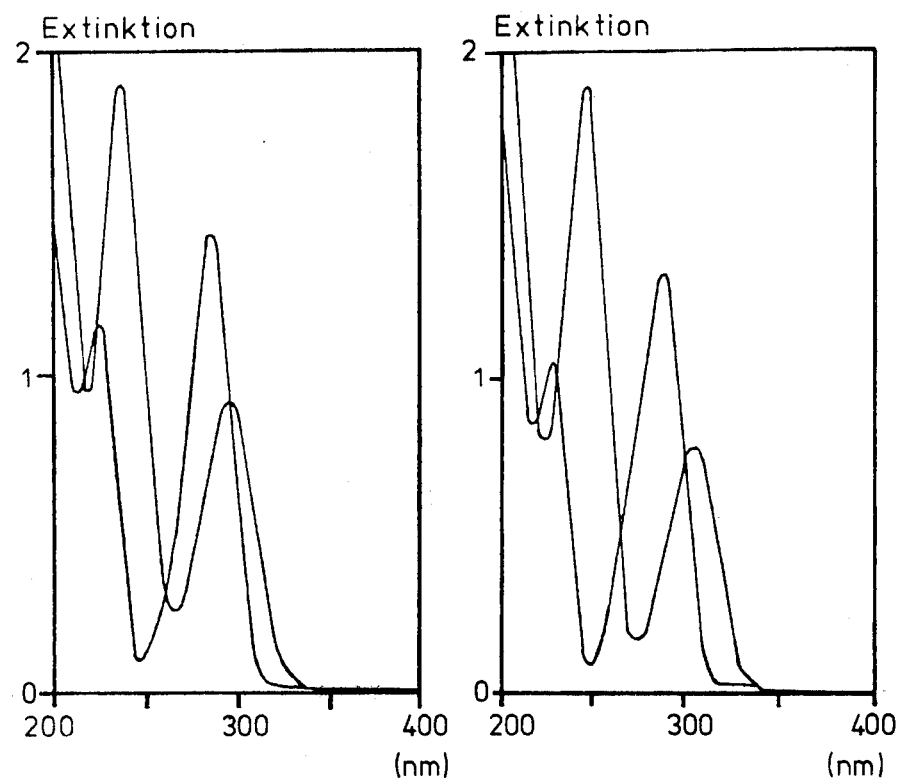
Figure 9:
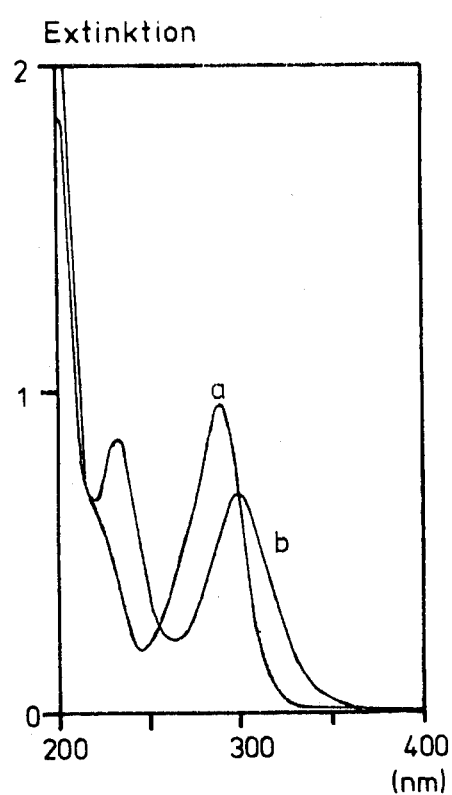
Figure 10:
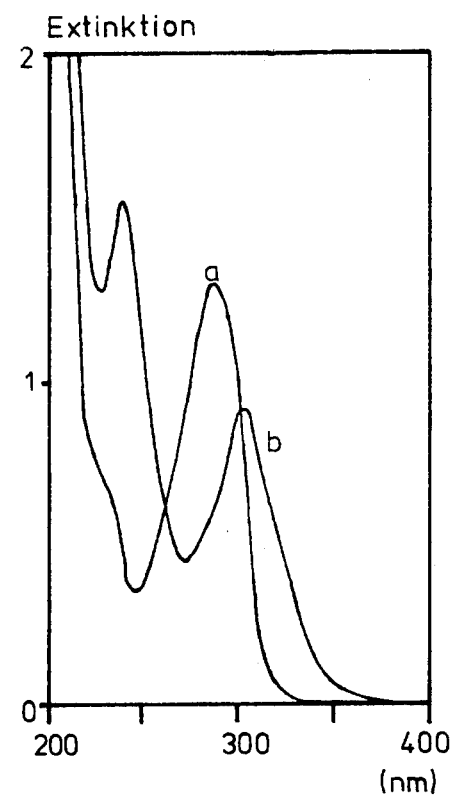
Figure 11:
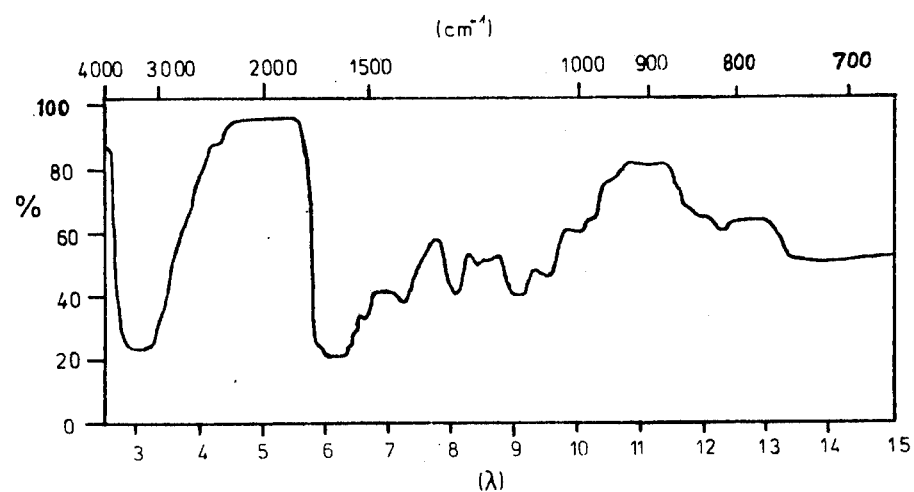
Figure 12:
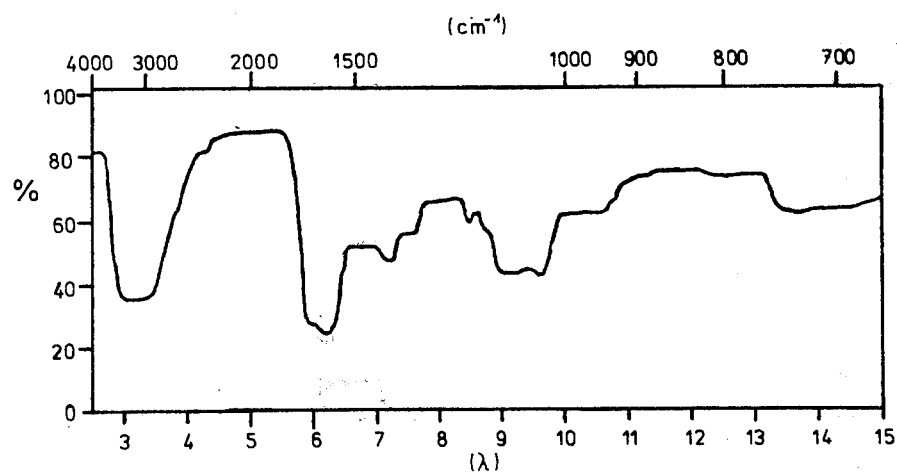
Figure 13:
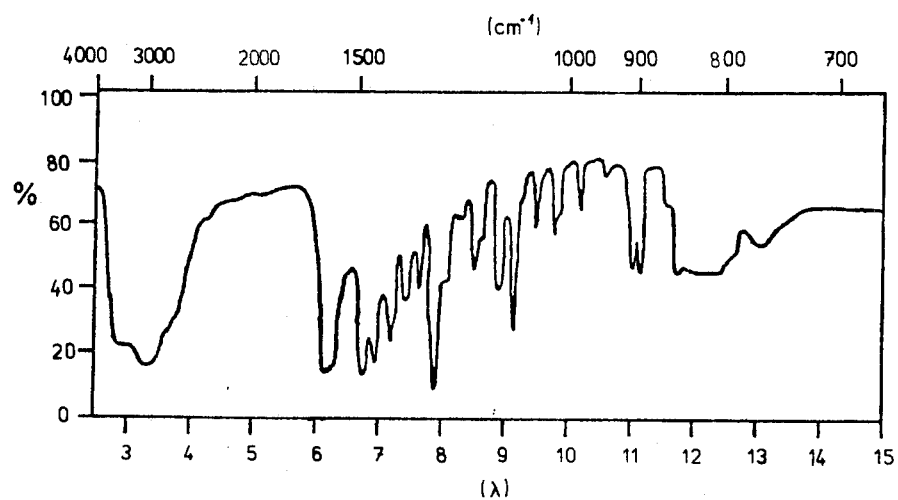
Figure 14:
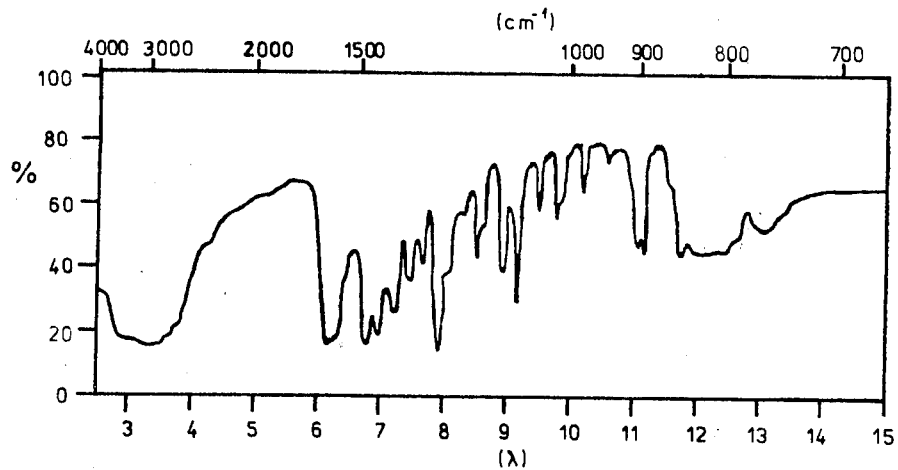
Figure 15:
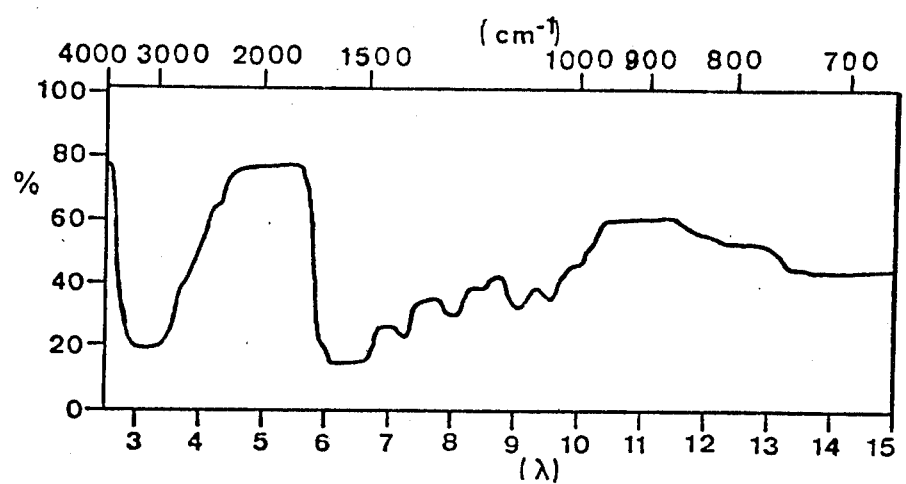
Figure 16:
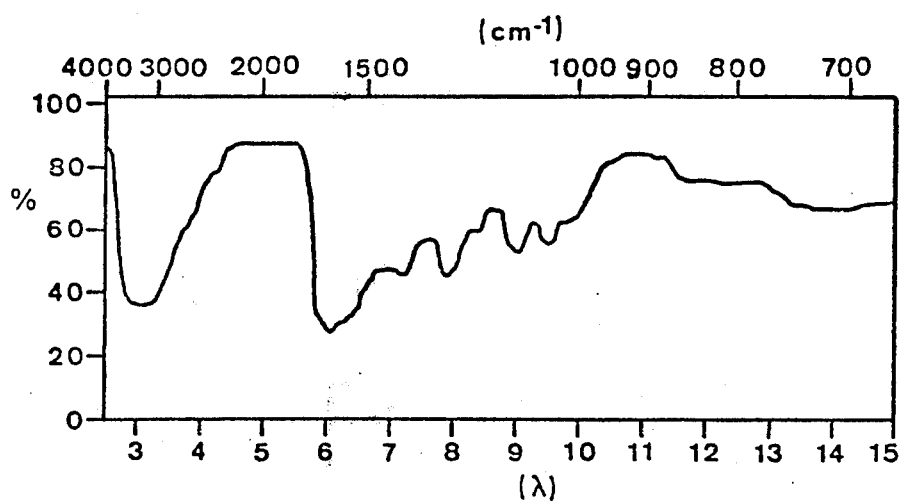
Figure 17:
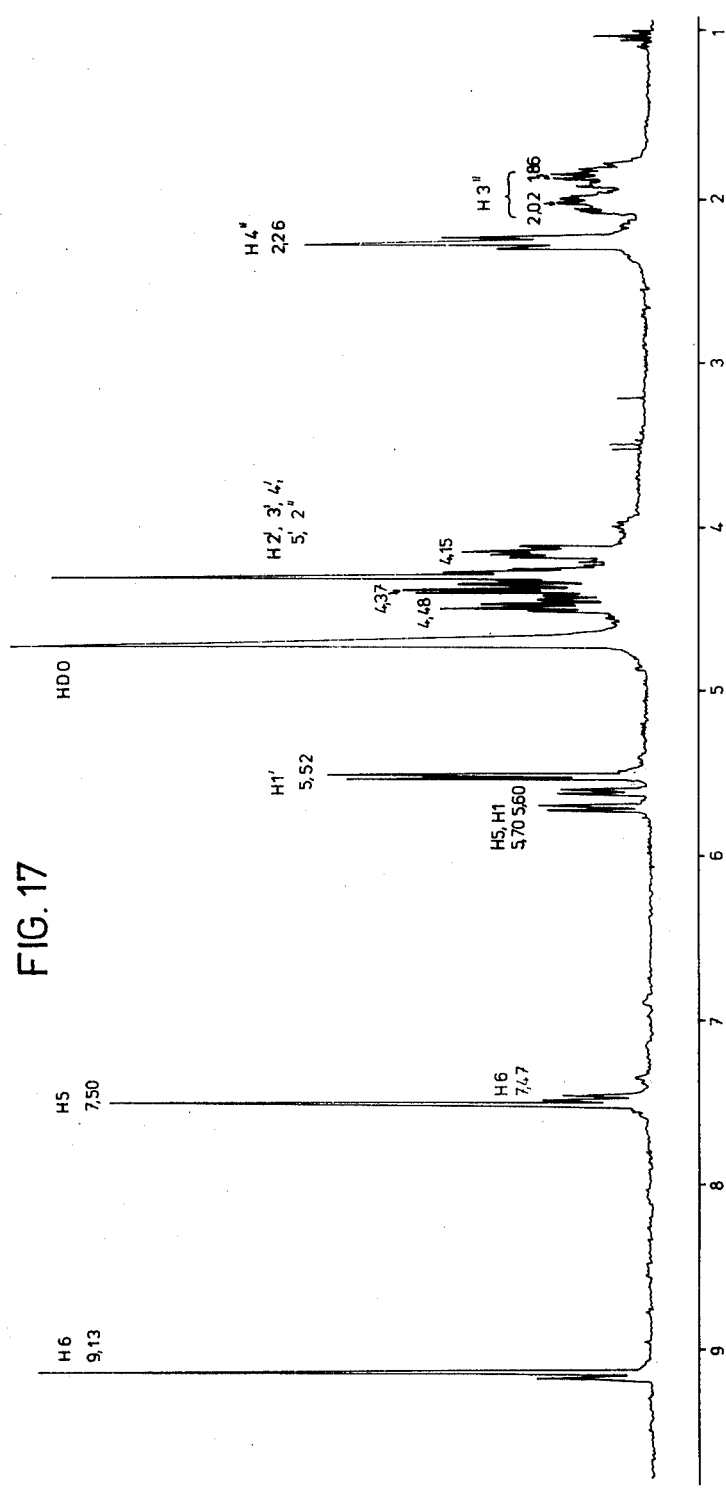
Figure 18:
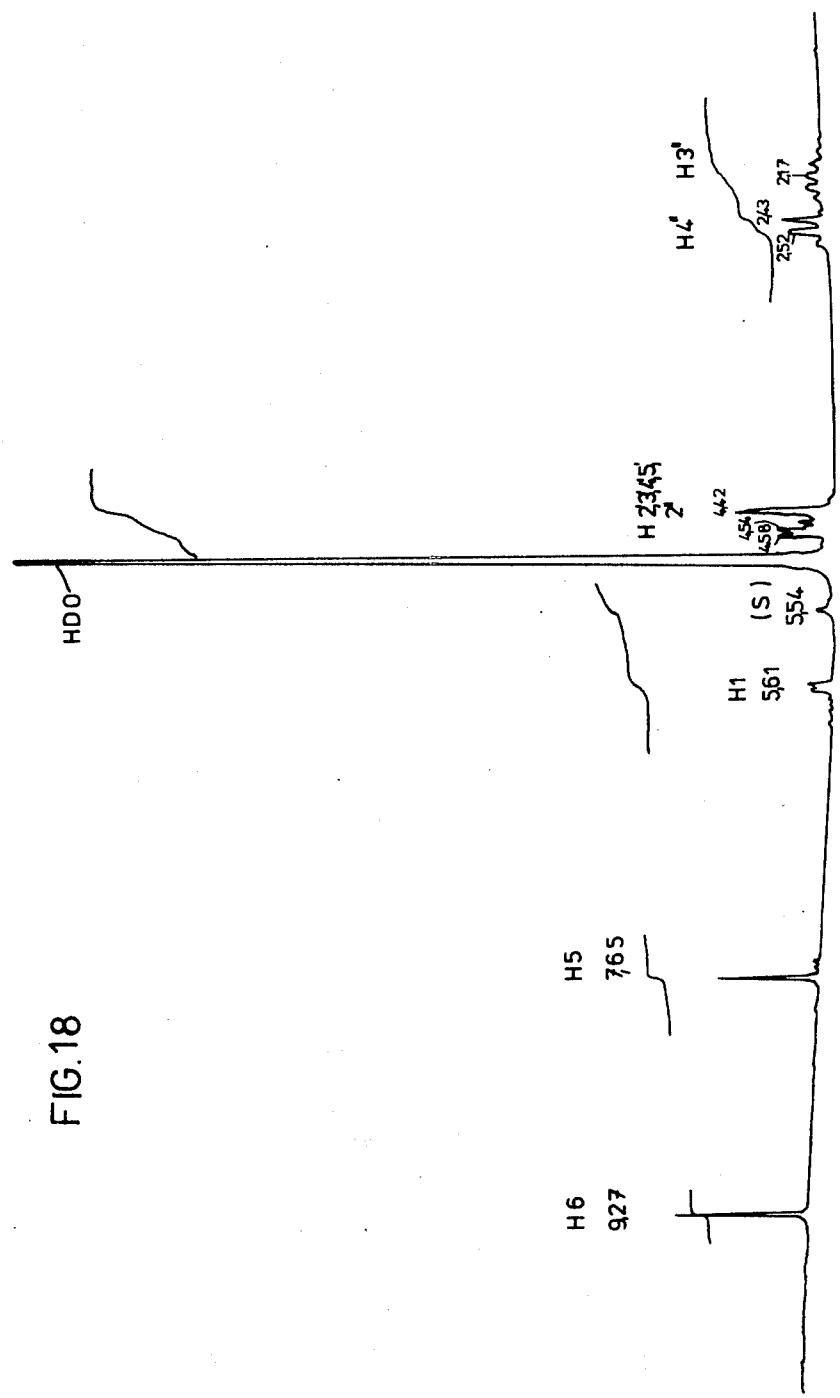

The invention will be further described with reference to the accompanying drawings wherein:

FIG. 1 is the UV spectrum of nikkomicin in HCl and NaOH;

FIG. 2 is the IR spectrum of nikkomicin in KBr;
FIG. 3 is an eluted diagram of nikkomicins I, J, Z and X from a Biogel PZ column;
FIG. 4 is an elution diagram of nikkomicins I, J, Z and X for a SP-sephadex C-25 column;
FIG. 5 is the UV spectrum of nikkomicin $B/B_x$;
FIG. 6 is the UV spectrum of nikkomicin $C/C_x$;
FIG. 7 is the UV spectrum of nikkomicin D;
FIG. 8 is the UV spectrum of nikkomicin E;
FIG. 9 is the UV spectrum of nikkomicin I/J;
FIG. 10 is the UV spectrum of nikkomicin Z/X;
FIG. 11 is the IR spectrum of nikkomicin $B/B_x$;
FIG. 12 is the IR spectrum of nikkomicin $C/C_x$;
FIG. 13 is the IR spectrum of nikkomicin D;
FIG. 14 is the IR spectrum of nikkomicin E;
FIG. 15 is the IR spectrum of nikkomicin I/J;
FIG. 16 is the IR spectrum of nikkomicin Z/X;
FIG. 17 is the NMR spectrum of nikkomicin M/N;
FIG. 18 is the NMR spectrum of nikkomicin M; and
FIG. 19 is a flow sheet of processes for the preparation of pure nikkomicin compounds and fractions.

Referring now more particularly to the drawings, the nikkomicin mixture, which is the subject of U.S. Pat. No. 4,046,881, can be characterized by the following data:

(a) Solubility and properties: nikkomicin is a colorless substance mixture which is very readily soluble in water and pyridine and insoluble in the other customary organic solvents. It exhibits a positive reaction with ninhydrin, sodium metaperiodate-benzidine and potassium permanganate. A yellow coloration is obtained with iron(III) chloride.

(b) The UV spectrum and the IR spectrum are available (see the corresponding diagrams in FIGS. 1 and 2). FIG. 1 shows the UV spectrum of nikkomicin, recorded (a) in 1 N hydrochloric acid and (b) in 0.1 N sodium hydroxide solution. The ordinates represent the extinction and the abscissae represent the wavelength (nm units). FIG. 2 shows the IR spectrum of nikkomicin, recorded in potassium bromide. The ordinates represent the transmission in % and the abscissae represent the frequency ($cm^{-1}$) and wavelength ($\mu m$ units).

(c) Uracil, an amino-hexuronic acid and a new aminoacid containing a pyridine ring could be detected with the aid of mass spectroscopy and chemical degradation by acid hydrolysis.

(d) Paper electrophoresis: The antibiotic is amphoteric. The migration distance is small around the pH value of 6, and the isoelectric point is thus probably here. The behavior of the nikkomicin mixture during electrophoresis is shown in the following table, in which the distances covered during paper electrophoresis are indicated as a function of the pH values of the buffer sysrem:

| Buffer | pH | Time (minutes) | Distance covered (mm) |
| --- | --- | --- | --- |
| Pyridine/glacial acetic acid | 3.9 | 60 | −12 |
| Pyridine/glacial acetic acid | 6.1 | 60 | −1 |
| 5,5-Diethyl-barbituric acid | 8.9 | 60 | +16 |

(e) Thin layer chromatography: In all the running agents used which contain acetic acid, three ninhydrin-positive spots appear here, and in each case only one spot corresponds to the substance which is active in the bioautogram. This fact could be attributed to the instability of the antibiotic in acetic acid solution. In neutral running agents, in each case only one ninhydrin-positive spot is found.

(f) The proposed structural formula for nikkomicin is:

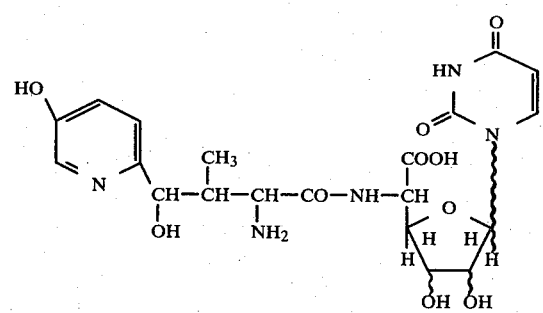

Elementary analysis of nikkomicin gave the following values: C 48.21%; H 5.08%; N 13.58% and O 31.58%. From these figures, an elementary composition of $C_4H_5NO_2$ is calculated. The molecular weight was determined cryoscopically as 404. The structure proposed here for nikkomicin, however, corresponds to a molecular weight of 495 and to the formula $C_{20}H_{25}N_5O_{10}=(C_4H_5NO)_5$. The elementary composition calculated from these figures is: C 48.49%; H 5.09%; N 14.14%; and O 32.39%.

(g) In contrast to the polyoxines known from the literature (see J. Am. Chem. Soc. 91, 7490 [1961]) which are closest to nikkomicin, the azacyclobutane radical is missing in nikkomicin. None of the polyoxines described contain the heterocyclic aminoacid.

The characteristics correspond to the statements in U.S. Pat. No. 4,046,881. As has since been found, they apply to a mixture of structurally different nikkomicins of the general formula

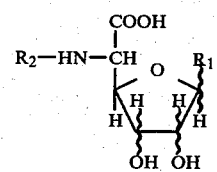

in which $R_1$ denotes

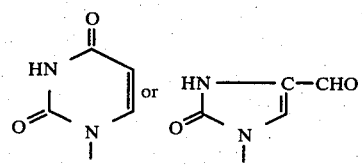

and $R_2$ denotes hydrogen,

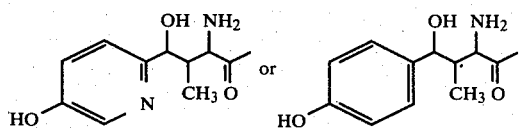

In particular, the following active-compound components of active-compound component pairs (a)

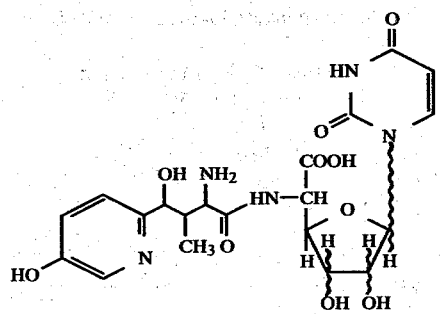   (Z)

and

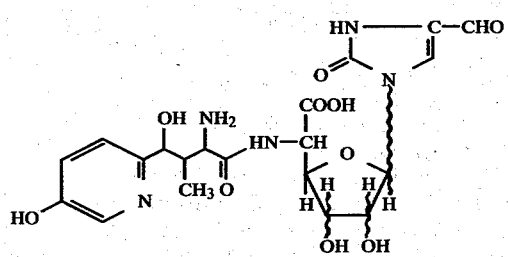   (X)

(b)

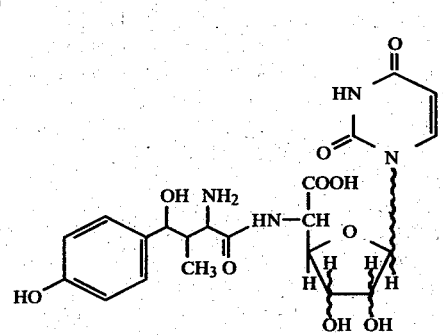   (B)

and

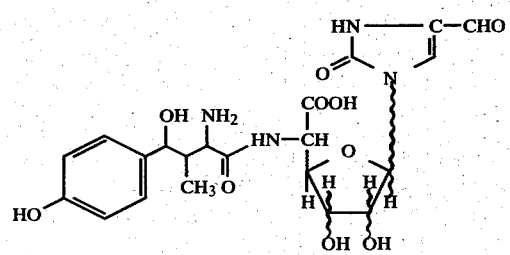   (B$_x$)

and (c)

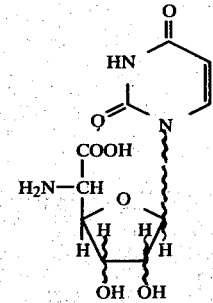

and

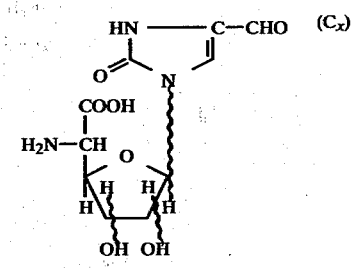   (C$_x$)

can be isolated from the nikkomicin mixture. These active-compound components and active compound component pairs are suitable as agents for combating agents. However, they are not the subject of the present invention.

Surprisingly, the nikkomicin mixture and its components or component pairs exhibit an excellent action against animal pests, in particular against insects and arachnids, coupled with a good toleration by plants and favorable toxicity to warm-blooded animals.

These active compounds exhibit a deterrent action on the eating activity and a delaying and inhibiting action on the development of insects. In the case of spider mites, slow eradication of a population is already achieved after a few treatments by using nikkomicin mixtures or nikkomicin components. In particular, depending on the time of application, an almost complete inhibition of the further development in the resting stages of nymphochrysalis, deutochrysalis and teleiochrysalis is obtained, an effect which was hitherto unknown with other naturally occurring substances or microbial metabolites. It is not necessary to add other active compounds with a synergistic or additive action. The nikkomicin mixtre and the components described above also have an outstanding action against phosphoric acid ester-resistant spider mites. The low oral toxicity to mammals (LD 50 in rats: >2,000 mg/kg) is a further advantage.

Further new components, which are likewise suitable as agents for combating pests, have now been isolated from the nikkomicin component mixture.

The invention thus provides, as new compounds, the nikkomicins of the formulae (C)

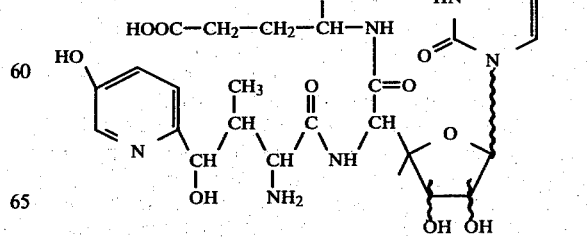

Nikkomicin I

-continued

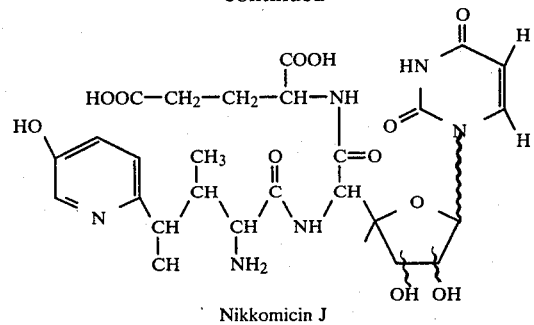

Nikkomicin J

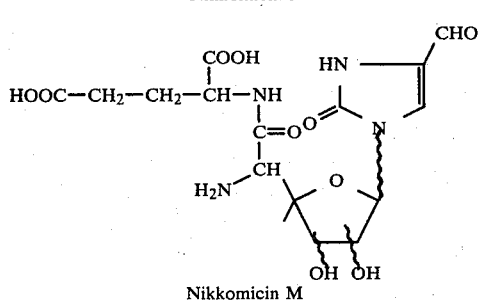

Nikkomicin M and

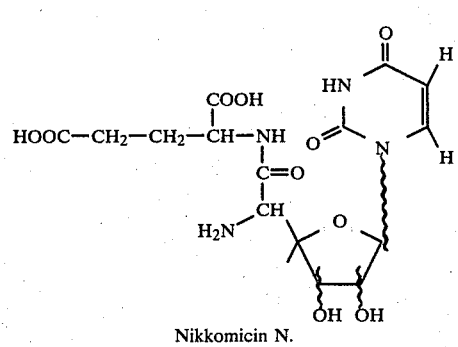

Nikkomicin N.

Moreover, the nikkomicin mixture also contains the components D and E, the structure of each of which is indicated below:

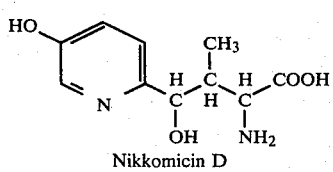

Nikkomicin D

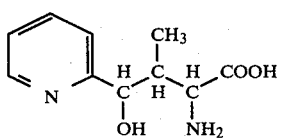

The invention furthermore relates to agents for combating pests, in particular insects and fungi. These agents contain the above-mentioned nikkomicins I, J, M, and N, eigher by themselves, as mixtures or as mixtures with one or more of the nikkomicins C, $C_x$, Z, X, B, $B_x$, D and E. This invention relates to each possible combination of the nikkomicins mentioned-with the exception of the combination D/E, and of the combinations $C/C_x$, Z/X and $B/B_x$, which have already been claimed in another patent application, and with the exception of the naturally occurring mixture—as agents for combating pests, and to their use for combating pests.

The invention relates, especially, to mixtures of nikkomicin I and nikkomicin J and of nikkomicin M and nikkomicin N, and to their use in and as agents for combating pests.

In general, the mixtures mentioned in each case consist of about 95% of I and about 5% of J, or of about 95% of M and about 5% of N, if they are prepared and isolated by the processes described below.

The individual nikkomicins can be characterized by the following data:

| UV Spectra | IR Spectra | NMR Spectra |
|---|---|---|
| FIG. 5 $B/B_x$ | FIG. 11 $B/B_x$ | FIG. 17 M/N |
| FIG. 6 $C/C_x$ | FIG. 12 $C/C_x$ | FIG. 18 M |
| FIG. 7 D | FIG. 13 D | |
| FIG. 8 E | FIG. 14 E | |
| FIG. 9 I/J | FIG. 15 I/J | |
| FIG. 10 Z/X | FIG.16 Z/X | |

$^1$H-NMR spectrum of the nikkomicins M and N:

The two singlets in the $^1$NMR spectrum of nikkomicin M and N (FIG. 17) at 9.13 and 7.50 ppm show that the mixture contains 4-formyl-4-imidazolin-2-one as a part structure. The doublet at 5.52 ppm (J=4.10 Hz), is to be allocated to the proton H-1' of the nucleoside I. The two doublets belonging to the uracil, at 7.47 ppm (J=7.91 Hz) and 5.70 ppm (J=7.91 Hz) and the doublet belonging to the H-1' of the nucleoside II, at 5.60 ppm (J=4.10 Hz) show that in this case also—as in the case of the nikkomicins Z and X, and I and J—both nucleosides are present. The multiplets at 2.02/1.86 ppm correspond to the two protons on C-3" of glutamic acid, which couple with the adjacent protons in the 4"- and 2"-position.

The triplet at 2.26 ppm is caused by the two H-4" protons, which couple with two protons in the 3"-position. The protons H-2', H-3', H-4', H-5' and H-2" of glutamic acid overlap in the region from 4.48 to 4.15 ppm. In comparison with free glutamic acid (3.81 ppm), the proton on the C-2" atom is shifted to a lower field by the peptidic linkage with the nucleoside.

After nikkomicin M has been isolated, analogously to nikkomicin X, with Alkylamine/CPG-1350, a glass support with 1-aminopropyl groupings, by doublets at 7.47, 5.70 and 5.60 ppm were missing and accordingly belong to nikkomicin N (FIG. 18). Thin layer chromatography:

The behavior of the nikkomicins on thin layer chromatography is shown in Table 1 below.

In running agent systems which contain glacial acetic acid, partial splitting of the substances into the nucleoside and aminoacid occurs during chromatography, as a result of which, after spraying which ninhydrin, 3 positive spots ($Rf_1$, $Rf_2$ and $Rf_3$) can be recognized. Only the spots at $Rf_2$ show the intact molecule.

TABLE 1

| Thin layer chromatography of the nikkomicins | | | | | |
|---|---|---|---|---|---|
| | | | | Rf-values | |
| | | | | c | |
| Nikkomicins | a | b | $Rf_1$ | $Rf_2$ | $Rf_3$ |
| $B/B_x$ | 0.86 | 0.38 | 0.22 | 0.58 | 0.72 |
| $C/C_x$ | 0.78 | 0.13 | | 0.22 | |
| D | 0.82 | 0.51 | | 0.67 | |
| E | 0.83 | 0.56 | | 0.66 | |
| I/J | 0.85 | 0.25 | 0.22 | 0.30 | 0.62 |

TABLE 1-continued

| Thin layer chromatography of the nikkomicins | | | | | |
|---|---|---|---|---|---|
| | | | Rf-values | | |
| Nikkomicins | a | b | $Rf_1$ | c $Rf_2$ | $Rf_3$ |
| Z/X | 0.84 | 0.27 | 0.22 | 0.32 | 0.67 | a Running agent: butanol/pyridine/$H_2O$ (1:1:1); silica gel
b Running agent: propanol/$H_2O$ (8:2); cellulose
c Running agent: ethanol/glacial acetic acid/water (4 1:1); cellulose

PAPER ELECTROPHORESIS

Table 2 shows the behavior of the nikkomicins on paper electrophoresis, as a function of the pH values of the buffer systems.

TABLE 2

| Electrophoretic behavior as a function of the pH value. | | | |
|---|---|---|---|
| | Distance covered (mm) | | |
| Nikkomicins | a | b | c |
| $B/B_x$ | −3 | 0 | +10 |
| $C/C_x$ | +2 | −2 | +11 |
| D | −4 | −6 | +12 |
| E | −6 | −4 | + 5 |
| I/J | −4 | 0 | +17 |
| Z/X | −6 | 0 | + 2 | a Pyridine/acetate buffer, pH 3.9
b Pyridine/acetate buffer, pH 6.1
c Borate/HCl buffer, pH 8.6

The active compounds are well tolerated by plants, have a favorable level of toxicity to warm-blooded animals, and can be used for combating arthropod pests, especially insects and acarids, and nematode pests which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber*;

from the class of the Diplopoda, for example *Blaniulus guttulatus*;

from the class of the Chilopoda, for example *Geophilus carpophagus* and Scutigera spec.;

from the class of the Symphyla, for example *Scutigerella immaculata*;

from the order of the Thysanura, for example *Lepisma saccharina*;

from the order of the Collembola, for example *Onychiurus armatus*;

from the order of the Orthoptera, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria*;

from the order of the Dermaptera, for example *Forficula auricularia*;

from the order of the Isoptera, for example Reticulitermes spp.;

from the order of the Anoplura, for example *Phylloxera vastatrix*, Pemphigus spp., *Pediculus humanus corporis*, Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci*;

from the order of the Heteroptera, for example Eurygaster spp., *Dysdercus intermedius, Piesma quadrata, Cimex lectularius, Rhodnius prolixus* and *Triatoma* spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Eupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella,* Agrotis spp., Euxoa spp., Feltia spp., *Earias insulana* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Ghoristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscerides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., *Fannia spp., Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example Scorpio maurus and *Latrodectus mactans;* from the order of the Acarina, for example Acarus siro, Argas spp., Ornithodoros spp., *Dermanyssus gallinae, Eriophyes ribis, Phyllocoptruta, oleivora,* Boophilus spp., Rhipicephalus spp., Amblyomma spp., Hyalomma spp., Ixodes spp., Psoroptes spp., Chorioptes spp., Sarcoptes spp., Tarsonemus spp.,

*Bryobia praetiosa,* Panonychus spp. and Tetranychus spp..

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp..

The active compounds according to the invention also exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

The good toleration, by plants, of the active compounds, at the concentrations required for combating plant diseases, permits treatment of above-ground parts of plants, of vegetative propagation stock and seeds, and of the soil.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvent, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations, or in the various use forms, as a mixture with other active compounds, such as fungicides, bactericides, insecticides, acaricides, nematicides, herbicides, bird repellants, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, immersion, spraying, atomizing, misting, vaporizing, injecting, brushing on, dusting, scattering, dry dressing, moist dressing, wet dressing, slurry dressing or encrusting.

Especially, in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, especially 0.01 to 10 g, are generally employed.

For the treatment of soil, active compound concentrations of 0.00001 to 0.1% by weight, especially 0.0001 to 0.02%, are generally employed at the place of action.

The present invention also provides a pesticidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids), nematodes, fungi or bacteria which comprises applying to the arthropods, nematodes, fungi or bacteria, or to a habitat thereof, a compound of the present invention alone or in the form of a composition containing as active ingredient a compound of the present invention in admixture with a diluent or carrier.

The present invention further provides crops protected from damage by arthropods, nematodes, fungi or bacteria by being grown in areas in which immediately prior to and/or during the time of the growing a compound of the present invention was applied alone or in admixture with a diluent or carrier.

It will be seen that the usual methods of providing a harvested crop may be improved by the present invention.

The following reagents, auxiliaries and technical instruments, some with trademarks, are mentioned in the following examples:

(a) Fermenters from New Brunswick Scientific Corporation Inc., New Brunswick, N.J. U.S.A.
(b) Hyphlo Supercel, trademark of Johns Manville, Cal., U.S.A.
(c) Filter presses C 150 and U 1000 from Schenck, Filterbau, Schwäbisch-Gmünd, Federal Republic of Germany
(d) Dowex, trademark of Dow Chemical Co., Midland, Michigan, U.S.A.
(e) Amterlite, trademark of Rohm and Haas Co., Philadelphia, Pa., U.S.A.,
(f) SP-Sephadex, trademark of Pharmacia Fine Chemicals, Upsala, Sweden.
(g) Uvicord II, LKB, Bromma, Sweden.
(h) Avicel, trademark of Merck.

PREPARATIVE EXAMPLES

Example 1

Preparation of the nikkomicin mixture

The nutrient solution in which the producer strain *Streptomyces tendae* Tü 901 was cultivated was composed of 2% of soya bean flour and 2% of mannitol; the pH was adjusted to pH 7.5 before the sterilization. 10×500 ml conical flasks which had 1 lateral inlet and each contained 100 ml of nutrient solution were inoculated with the producer strain and incubated at 27° C. for 48 hours on a rotating shaking machine, at 120 revolutions/minute. A 10 liter fermenter ("New Brunswick") which contained 10 liters of nutrient solution was inoculated with this preculture and was incubated at 27° C. for 48 hours, at 220 revolutions/minute and with an air supply of 4 liters/minute. A 100 liter fermenter ("New Brunswick"), which contained 100 liters of nutrient solution, was inoculated with this pre-fermenter material and was incubated at 27° C. for 78 hours, at 150 revolutions/minute and with an air supply of 450 liters/minute.

The culture was pressed off, with the addition of 2% of a filtration auxiliary (Hyphlo Supercel, Johns Mansville) and using a filter press, first over a preclarification filter (C 150, Schenk) and then over a post-clarification filter (U 1000, Schenk). The clear culture filtrate was acidified to pH 4.0 with acetic acid and discharged onto a column (100×450 mm) packed with Dowex 50 W×4 (50−100 mesh, Na+ form). The flow rate was 10 liters/hour. The column was washed with deioni ed water until the liquid issuing from the column was completely colorless. The antibiotic acid eluted with in each case 30 liters of 0.01 N ammonia and 0.05 N ammonia. The biologically active eluate was freed from ammonia on a rotary evaporator, acidified to pH 4.0 with acetic acid and discharged onto a column (70×900 mm) packed with "Amberlite 252" (Na+ form). The flow rate was 5 liters/hour. The column was washed with deionized water until the liquid issuing from the column was completely colorless. The antibiotic was eluted with 15 liters of 0.05 N ammonia. The biologically active eluate was freed from ammonia on a rotary evaporator and concentrated to a small volume (1 liter) and the concentrate was acidified to pH 4.0 with acetic acid and discharged onto a column (25×850 mm) packed with SP-Sephadex C-25. The flow rate was 100 ml/hour. The column was washed with deionized water until absorption was no longer indicated at 280 nm in a UV flow detector (Uvicord II, LKB). Impurities were eluted with 0.01 M pyridine/acetate buffer (pH 4.7) and the antibiotic was eluted with 0.02 M pyridine/acetate buffer (pH 4.7). The biologically active fractions were combined, freed from buffer on a rotary evaporator and concentrated to a very small volume. The concentrate (10 ml) was discharged onto a column (25×1500 mm) packed with Biogel P 2 (200-400 mesh) and eluted with deionized water. The flow rate was 100 ml/hour. To monitor the purity, the eluate was examined at 280 nm with a UV flow detector. The biologically active fractions were combined and lyophilized in a freeze-drying unit.

The isolation of the nikkomicin components Z and X from the nikkomicin mixture thus prepared is described in the following text.

EXAMPLE 2

Isolation of nikkomicin Z 10 ml of a saturated, aqueous dimedone solution were added to 100 mg of nikkomicin and the mixture was warmed to 50°-70° C. on a waterbath for 10 minutes and then left to stand at room temperature for 20 hours. After evaporation in a rotary evaporator, the residue was taken up in 1 ml of $H_2O$ and the mixture was chromatographed on a column (0.9×60 cm) containing cellulose (Avicel, Messrs Merck) using running agent system A. The orange-red dimedone derivative of X was eluted, together with excess dimedone, before Z. The fractions containing Z were combined and rechromatographed on the same column. Yield: 11.4 mg of Z. System A: ethanol/acetic acid/water (4:1:1-volume).

EXAMPLE 3

Isolation of nikkomicin X 19 g of nikkomicin were dissolved in 75 ml of $H_2O$, and 9 g of Alkylamine/CPG-1350 (Pierce Chem. Comp.) were added. After degassing the mixture in vacuo, it was left to stand at room temperature for 24 hours. The support material was filtered off, washed out with 800 ml of $H_2O$ and treated with 100 ml of 5% strength acetic acid at room temperature for 30 minutes. The filtrate was lyophilized. 116 mg of a residue, which was subsequently chromatographed on LiChroprep RP-8 using methanol/$H_2O$ (30:70), were obtained. Yield of X (after lyophilization): 18 mg.

EXAMPLE 4

Determination of the ratio between nikkomicin X and Z (a) By means of $^1$H-NMR spectroscopy Nikkomicin Z can be recognized in the $^1$H-NMR spectrum by the two protons, which couple with one another, in the 5-position ($\delta=5.91$; d; 8 Hz) and the 6-position ($\delta=7.59$; d; 8 Hz). These two resonances are missing in nikkomicin X. Instead, two singlets occur at $\delta=7.69$ and $\delta=9.33$. It is possible to determine the ratio between nikkomicin X and Z in the mixture by comparison of the integrals of these signals.

(b) By means of high performance liquid chromatography.

The two nikkomicins X and Z can be separated on a LiChroprep RP-18 column (Merck, 10 and 250×4.6 mm) using a 0.005 molar solution of 1-hexanesulphonic acid in methanol/H$_2$O/acetic acid (14/84/2) as the eluting agent, and they can be determined quantitatively by means of UV detection at 280 nm. This determination can be effected directly from the culture filtrate.

Further processes for the isolation and characterization of nikkomicins

Processes for the preparation of pure substances from cultures of *Streptomyces tendae* are shown in the FIG. 19.

EXAMPLE 5

Isolation of the nikkomicins I/J, Z and X

The culture (20 liter fermenter) was pre-clarified, after adding 2% of celite and using a multi-layer filter press, over the filter layer C 150 (Schenk Filterbau, Schwäbisch Gmünd). The culture filtrate was adjusted to pH 4 with acetic acid and post-clarified over the filter layer U 1000 using a multi-layer filter press.

The clear culture filtrate was discharged onto a column packed with Dowex 50WX4 (50–100 mesh, Na$^+$ form) (volume of bed: 3 liters, flow rate: 7 liters/hour). The column was washed with deionized water until the liquid issuing from the column was completely colorless. Impurities were eluted with 0.01 N NH$_3$ solution and the nikkomicin mixture was eluted with 0.05 N NH$_3$ solution. The biologically active eluate was freed from ammonia in vacuo and acidified to pH 5.5 with formic acid.

The eluate treated in this manner was discharged onto a column packed with Amberlite IRC-84 (Na$^+$ form) (volume of the bed: 2 liters flow rate: 5 liters/hour). The column was washed with an amount of water three times the volume discharged onto the column. The material bonded to the IRC-84 was eluted with a 1 N HCOOH/CH$_3$OH mixture (1+9) and was concentrated to a small volume in vacuo.

The concentrate was discharged onto a column packed with SP-Sephadex C-25 (pyridinium form) (volume of the bed: 1 liter, flow rate: 100 ml/hour). The column was washed with deionized water until absorption at 280 nm was no longer indicated in a UV detector (Unicord II, LKB, Bromma, Sweden). Impurities were eluted with 0.01 N pyridine/acetate buffer and the nikkomicins I/J, X and Z were eluted with 0.05 N pyridine/acetate buffer (pH 4.7).

The biologically active fractions were combined, freed from buffer in vacuo and concentrated to a small volume and the concentrate was lyophilized in a freeze-drying unit. The product thus obtained was purified, in small portions (300–400 mg), by gel chromatography on Biogel P2 (200–400 mesh, volume of the bed: 1 liter, flow rate: 60 ml/hour). Separation into nikkomicin I/J and the naturally occurring nikkomicin Z/X mixture was achieved. The appropriate fractions were combined and concentrated and the concentrate was lyophilized. The nikkomicin Z/X mixture obtained consisted of 90% of nikkomicin X and 10% of nikkomicin Z, determined by the dimedone reaction. The yield from a 20 liter fermenter was 25% of the amount present in the culture filtrate, so that in the case of a production of 1.3 g/l, about 5 g of pure nikkomicin Z/X mixture could be isolated.

Pure nikkomicin I/J could be isolated with a yield of about 0.8 g.

FIG. 3: Elution diagram of the Biogel P2 column

UV absorption at 280 nm Activity against Mucor hiemalis (±)

Peak 1: yellow dyestuff; Peak 2: nikkomicin I/J, Peak 3: nucleoside part of nikkomicin Z/X; Peak 4: aminoacid part of nikkomicin Z/X; Peak 5: nikkomicin Z/X

EXAMPLE 6

Isolation of the nikkomicins B/B$_x$ and C/C$_x$

The runnings and the wash water from the Amberlite IRC-84 column (about 10% of the activity discharged onto the column) were combined and discharged onto a column packed with Dowex 50WX4 (Na$^+$ form, 50–100 mesh) (volume of the bed: 700 ml, flow rate: 3 liters/hour). Impurities were eluted with 0.01 N NH$_3$ solution and the nikkomicin mixture was eluted with 0.03 N NH$_3$ solution. The active eluates were combined and freed from ammonia in a rotary evaporator, the pH was adjusted to 4.7 with acetic acid and the mixture was discharged onto a column packed with SP-Sephadex C-25 (volume of the bed: 500 ml, flow rate: 100 ml/hour). The column was washed with deionized water until absorption at 280 nm was no longer indicated in a UV detector. The runnings and the wash water contained the nikkomicins B/B$_x$ and C/C$_x$. The runnings and the wash water were combined and concentrated to a very small volume and the concentrate was chromatographed over Biogel P2 (50–100 mesh, bed volume: 1 liter, flow rate: 150 ml/hour). Separation into nikkomicin C/C$_x$ and B/B$_x$ was achieved. Overlapping fractions were rechromatographed. Further purification of the nikkomicins was then effected by gel chromatography on Biogel P2 (100–200 mesh, volume of the bed: 500 ml, flow rate: 80 ml/hour). To isolate the pure substance, reversed phase chromatography on LiChroPrep RP8 (particle size: 20–40μ, volume of the bed: 250 ml, flow rate: 60 ml/hour) was carried out. Deionized water was used as the running agent.

The yield (20 liter fermenter) of nikkomicin C/C$_x$ mixture was 350 mg. The mixture was composed of 10% of nikkomicin C and 90% of nikkomicin C$_x$.

120 mg of nikkomicin B/B$_x$ could be isolated. Only traces of the component nikkomicin B were present in the nikkomicin B/B$_x$ mixture.

EXAMPLE 7

Isolation of nikkomicin D, E, I/J and Z/X

The nikkomicins D, E, I/J and Z/X were bonded to the SP-Sephadex C-25 column described in Example 6. Nikkomicins D and E, in separate peaks, and the nikkomicins I/J, Z and X, in a common peak, were eluted with 0.03 N pyridine/acetate buffer. The nikkomicins D and E could be purified, after removing the pyridine/acetate buffer and concentrating in vacuo, on Biogel P2 (100–200 mesh, volume of the bed: 500 ml, flow rate: 80 ml/hour).

The yield of nikkomicin D was 180 mg and the yield of nikkomicin E was 130 mg.

The nikkomicins I/J and Z/X could be separated and purified as described in Example 5.

From a quantitative point of view, the yield of the nikkomicins I/J and Z/X isolated in this way was about one tenth of the yield isolated in Example 5. FIG. 4: Elution diagram of the SP-Sephadex C-25 column with 0.03 N pyridine/acetate buffer UV absorption at 280 nm Activity against Mucor hiemalis (±)

Peak 1: nikkomicin D; Peak 2: nikkomicin E; Peak 3: nikkomicins I/J and Z/X.

EXAMPLE 8

Isolation of nikkomicin M/N

The nikkomicins M/N were formed from the nikkomicin I/J mixture by hydrolysis.

200 ml of water and 200 ml of 0.02 M phosphate buffer, pH 7.3, were added to 14 g of nikkomicin mixture (about 30% strength, according to the biological activity) and the mixture was left to stand at 37° C. for 8 days. After acidifying to pH 2.2 with acetic acid, the solution was discharged onto a column packed with AG 50 W-X8 (H+ form; 50–100 mesh; Biorad; 90×4 cm). The column was eluted with a linear gradient of in each case 2 liters of pyridine/acetate buffer (0.2 M; pH 3.1 and 2 M; pH 5.0). The nucleosides C/$C_x$, nikkomicin M/N and nikkomicin E were first eluted together, and then nikkomicin D was eluted.

The fractions containing nikkomicin D were concentrated and the concentrate was taken up in water. On neutralization, a finely powdered white precipitate was formed, and was centrifuged off and recrystallized from hot water.

Fractions containing the nucleosides, nikkomicin M/N and nikkomicin E were concentrated, the concentrate was taken up in water, the mixture was discharged, in 2 portions, onto a cellulose column (2.5×100 cm) packed with Avicel, Messrs Merck, and the components were eluted with ethanol/glacial acetic acid/water (4:1:1), in the following sequence: nikkomicin E, nikkomicin M/N, nucleoside C, nucleoside $C_x$. Yields: nikkomicin D: 1.05 g (crystals), 817 mg (freeze-dried), nikkomicin E: 405 mg, nikkomicin M/N: 1.27 g (freeze-dried), nucleoside C: 284 mg (crystals)+317 mg (freeze-dried) and nucleoside C/$C_x$: 800 mg (freeze-dried).

It will be appreciated that the instant specification and examples are set forth by way of illustration and not limitation, and that various modifications and changes may be made without departing from the spirit and scope of the present invention.

What we claim is:

1. A pure nikkomicin selected from the group consisting of

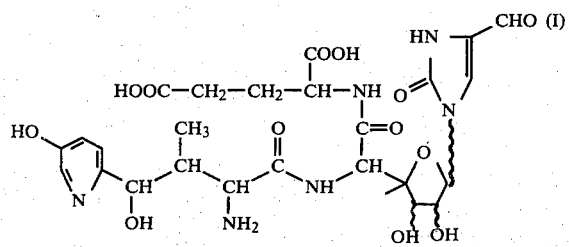

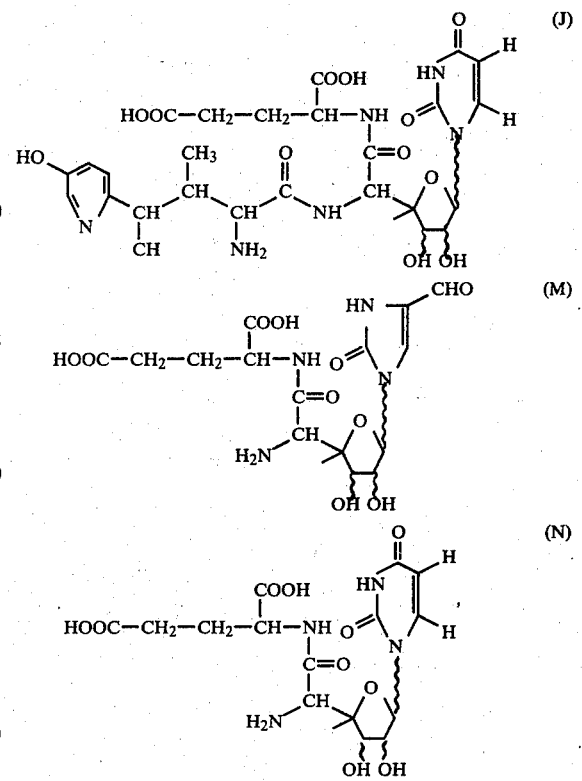

a mixture of nikkomicin I and J, and a mixture of nikkomicin M and N.

2. A nikkomicin according to claim 1 consisting essentially of pure

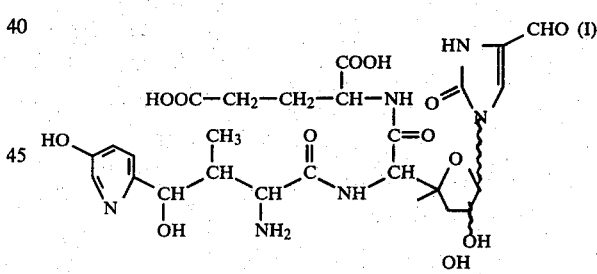

3. A nikkomicin according to claim 1 consisting essentially of pure

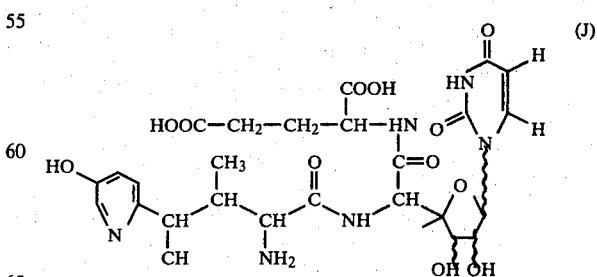

4. A nikkomicin according to claim 1 consisting essentially of pure

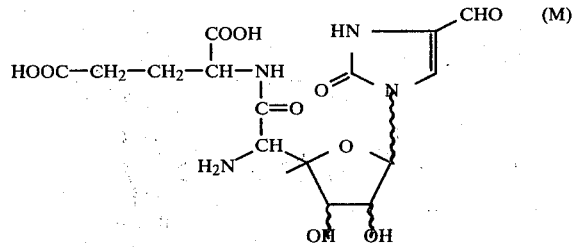

5. A nikkomicin according to claim 1 consisting essentially of pure

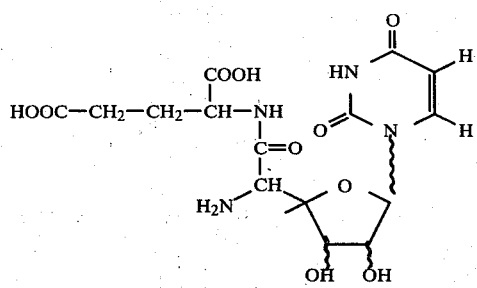

6. A nikkomicin according to claim 1 consisting essentially of a pure mixture of

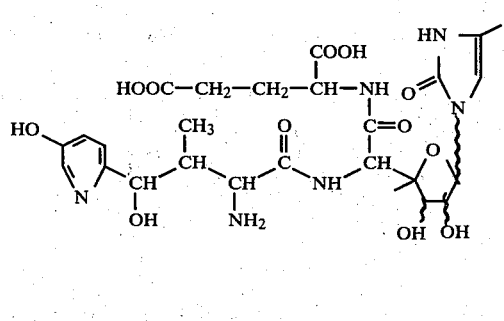

and

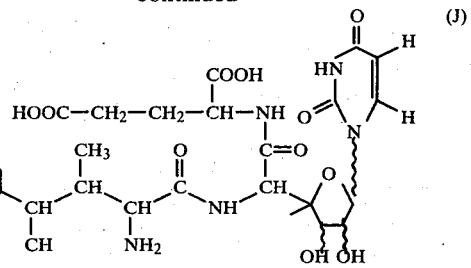

7. A nikkomicin according to claim 1 consisting essentially of a pure mixture of

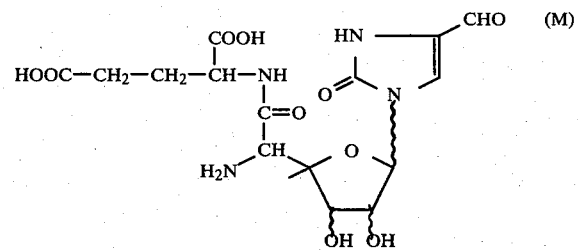

and

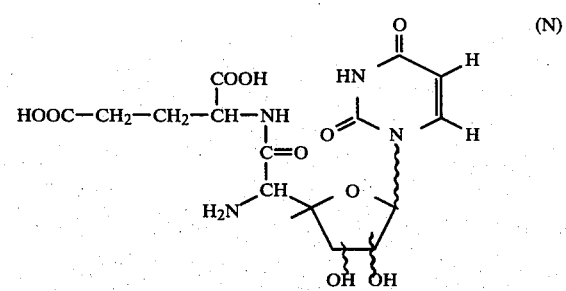

8. A pesticidal composition comprising a pesticidally effective amount of a nikkomicin according to claim 1 in admixture with a diluent.

9. A method of combating pests selected from the group consisting of arthropods, nematodes, fungi and bacteria which comprises applying to the pests, or to a habitat thereof, a pesticidally effective amount of a nikkomicin according to claim 1.

10. The method according to claim 9 wherein said pests are arthropods or nematodes.

11. The method according to claim 9 wherein said pests are fungi.

12. The method according to claim 9 wherein said pests are bacteria.

* * * * *